United States Patent
Smith, Jr. et al.

(10) Patent No.: US 7,449,612 B2
(45) Date of Patent: Nov. 11, 2008

(54) PARAFFIN ALKYLATION PROCESS

(75) Inventors: Lawrence A. Smith, Jr., Houston, TX (US); William M. Cross, Jr., Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 189 days.

(21) Appl. No.: 11/402,079

(22) Filed: Apr. 11, 2006

(65) Prior Publication Data

US 2007/0238912 A1    Oct. 11, 2007

(51) Int. Cl.
    *C07C 2/58* (2006.01)
(52) U.S. Cl. .......... 585/716; 585/717; 585/719
(58) Field of Classification Search ......... 585/716, 585/717, 719
    See application file for complete search history.

(56) References Cited

U.S. PATENT DOCUMENTS

| | | |
|---|---|---|
| 3,236,912 A * | 2/1966 | Phillips ............ 585/331 |
| 5,003,124 A | 3/1991 | Smith, Jr. et al. |
| 5,583,275 A | 12/1996 | Kranz et al. |
| 5,648,586 A | 7/1997 | Sampath |
| 5,649,281 A | 7/1997 | Sampath |
| 6,194,625 B1 | 2/2001 | Graves et al. |
| 6,995,296 B2 | 2/2006 | Smith, Jr. et al. |
| 7,145,049 B2 | 12/2006 | Loescher et al. |
| 7,250,542 B2 | 7/2007 | Smith, Jr. et al. |
| 7,273,957 B2 | 9/2007 | Bakshi et al. |

OTHER PUBLICATIONS

Albright, Lyle F., Kranz, Ken E., Alkylation of Isobutane with Pentenes Using Sulfuric Acid as a Catalyst . . . , Ind. Eng. Chem. Res. 1992, 31, 475-481, American Chemical Society.

* cited by examiner

*Primary Examiner*—Thuan Dinh Dang
(74) *Attorney, Agent, or Firm*—Osha Liang LLP (57) ABSTRACT

A process for the alkylation of isobutane is disclosed wherein isobutane is fed to two separate alkylation systems. The effluent from the first alkylation system is fed to an interim debutanizer where the $C_4$'s are separated from the alkylate product. The overhead $C_4$ product is then fed to the second alkylation system to provide the isobutane. The effluent from the second alkylation system is fed to a traditional deisobutanizer to prevent any build up of normal butanes in the system.

24 Claims, 4 Drawing Sheets

PARAFFIN ALKYLATION PROCESS

BACKGROUND OF THE INVENTION

1. Field of the Invention

The present invention relates to the alkylation of paraffinic hydrocarbon feed stocks wherein an olefin is reacted with isobutane to produce an alkylate product. More particularly the invention relates to a process wherein an intermediate debutanizer is utilized between two alkylation systems to provide a first alkylate product and a concentrated isobutane stream for use in a the second alkylation system. The process eliminates the need for a second deisobutanizer.

2. Related Information

Alkylation is the reaction of a paraffin, usually isoparaffins, with an olefin in the presence of a strong acid which produces paraffins, e.g., of higher octane number than the starting materials and which boil in range of gasolines. In petroleum refining the reaction is generally the reaction of a $C_3$ to $C_5$ olefin with isobutane.

In refining alkylations, hydrofluoric or sulfuric acid catalysts are most widely used. For sulfuric acid catalyzed alkylation low temperature or cold acid processes are favored because side reactions are minimized. In the traditional process the reaction is carried out in a reactor where the hydrocarbon reactants are dispersed into a continuous acid phase. In view of the fact that the cold acid process will continue to be the process of choice, various proposals have been made to improve and enhance the reaction and, to some extent, moderate the undesirable effects.

SUMMARY OF THE INVENTION

Briefly the present invention is an alkylation process which utilizes an interim debutanizer or stripper between at least two or more alkylation systems, preferably a process for the alkylation of isobutane with an olefin comprising a first and second alkylation systems wherein the effluent from the first alkylation system is fed to a debutanizer to produce an overhead and a first alkylation product, and wherein the overhead is fed to the second alkylation system. The capital investment benefits and energy consumption benefits, provided by the new processing scheme stem from the ability of having or producing a predominantly n-butane free olefin feedstock to be used in a first alkylation system or unit. This allows for significantly increased alkylation production without the traditional expense of additional deisobutanizer capacity, while still maintaining high quality motor-fuel alkylate production. As such, it provides refiners a new option for retrofitting existing equipment for use in expanding their facility alkylation capacity.

Two general process schemes are presented. The first general process scheme involves the use of two alkylation systems and requires an oligomerization reactor and a smaller distillation or stripping column for separation of $C_4$'s from heavier $C_5$+ materials. The first option can allow for significant reuse of equipment previously utilized for MTBE production. The second major scheme allows for processing either $C_3$'s or $C_5$'s in a first alkylation system with an interim debutanizer and processes $C_4$'s in a secondary alkylation system with a deisobutanizer. Several variations to the two general process schemes exist, especially for cases where alkylation of $C_3$ through $C_5$ olefin containing feedstocks is desired.

The key herein, to be able to off-load the need for additional deisobutanizer capacity, is in obtaining a nearly n-butane free olefin feed stream which may be used during an intermediate alkylation stage. This eliminates the majority of n-butane to this intermediate alkylation stage which in turn eliminates the need for an additional isobutane/n-butane fractionation step (deisobutanizer).

In one embodiment the process for the alkylation of isobutane with an olefin comprises:

(a) feeding a first stream containing isobutane and a second stream containing an olefin, preferably an FCC $C_4$ stream containing normal butene, isobutene, normal butane and isobutane; or a mixture of: $C_4$ and $C_5$ olefins; $C_3$ and $C_4$ olefins; or $C_3$, $C_4$ and $C_5$ olefins, to a first alkylation system where a portion of the isobutane is reacted with a portion of the olefin to form an alkylate containing stream;

(b) feeding the effluent from the first alkylation system to a debutanizer where $C_4$'s are removed as a first overheads and a first alkylate product is removed as a first bottoms;

(c) feeding the first overheads and a third stream containing isobutane to a second alkylation system where isobutane is reacted with $C_4$ olefins in said first overheads to form a second alkylate product.

DETAILED DESCRIPTION OF THE INVENTION

As herein defined an individual alkylation system comprises all the necessary equipment for production of a dilute alkylate stream from an olefin containing stream and an isobutane rich stream. Sulfuric acid, hydrofluoric acid and solid acid catalyst alkylation processes are contemplated. Such systems are well known in the art.

Olefin feed streams utilized herein may be hydrotreated to remove dienes prior to entering the alkylation process. The removal of butadienes and pentadienes is an important element in increasing catalyst life in the alkylation process. For processes which include oligomerization reactors to provide a purified oligomer product, the hydrotreatment step may be included (using reactive distillation) in the distillation column used to produce the oligomer stream. For feeds to oligomerization reactors, the removal of basic compounds is required to maintain catalyst life. For butylene containing streams this may include the use of a water wash column for removal of nitriles. Catalysts used in oligomerization reactors may be acid resins, such as Amberlyst 15 or related oleum derived resins and may include phosphoric acid derived catalysts, such as those known to the industry as SPA (solid phosphoric acid) catalysts.

Alkylation With $C_4$ Olefin Feedstock

In this case the means for obtaining the high purity olefin feed from a fluid catalytically cracked (FCC) $C_4$ feedstock is through the step of oligomerization, which is characterized as a process for the alkylation of isobutane with butenes contained in an FCC $C_4$ stream comprising the steps of:

(a) feeding a first stream comprising an FCC $C_4$ stream containing normal butenes and isobutenes to an oligomerization reaction wherein the isobutenes react with each other to produce an effluent containing $C_5$ and higher oligomers and normal butenes;

(b) fractionally distilling the effluent from the oligomerization reaction wherein the $C_4$ and lighter material is separated as a first overheads from the $C_5$ and heavier material as a first bottoms;

(c) feeding the first bottoms and isobutane to a first alkylation zone to produce a first alkylate stream containing alkylate and unreacted $C_4$'s;

(d) feeding the first alkylate stream to a debutanizing zone wherein the unreacted $C_4$'s are removed as a second overheads and alkylate product is removed as a second bottoms;

(e) feeding the first overheads and isobutane to a second alkylation zone wherein the olefins in the first overheads are reacted with isobutane to produce a second alkylate stream containing alkylate, unreacted isobutane and unreacted normal butane;

(f) feeding the second alkylate stream to a deisobutanizing zone wherein isobutane is removed as a third overheads, alkylate is removed as a third bottoms and normal butane is removed as a side stream.

Optionally, the third overheads may be combined with make-up isobutane and co-fed said first stream as feed to the oligomerization reaction; and/or optionally the fractionator for separating $C_4$'s from the oligomers contains a bed of hydrogenation catalyst and hydrogen is fed to the fractionator such that dienes contained within said effluent are hydrogenated simultaneously with the separation. Fresh isobutane may be fed to said second alkylation zone.

Figure 1:
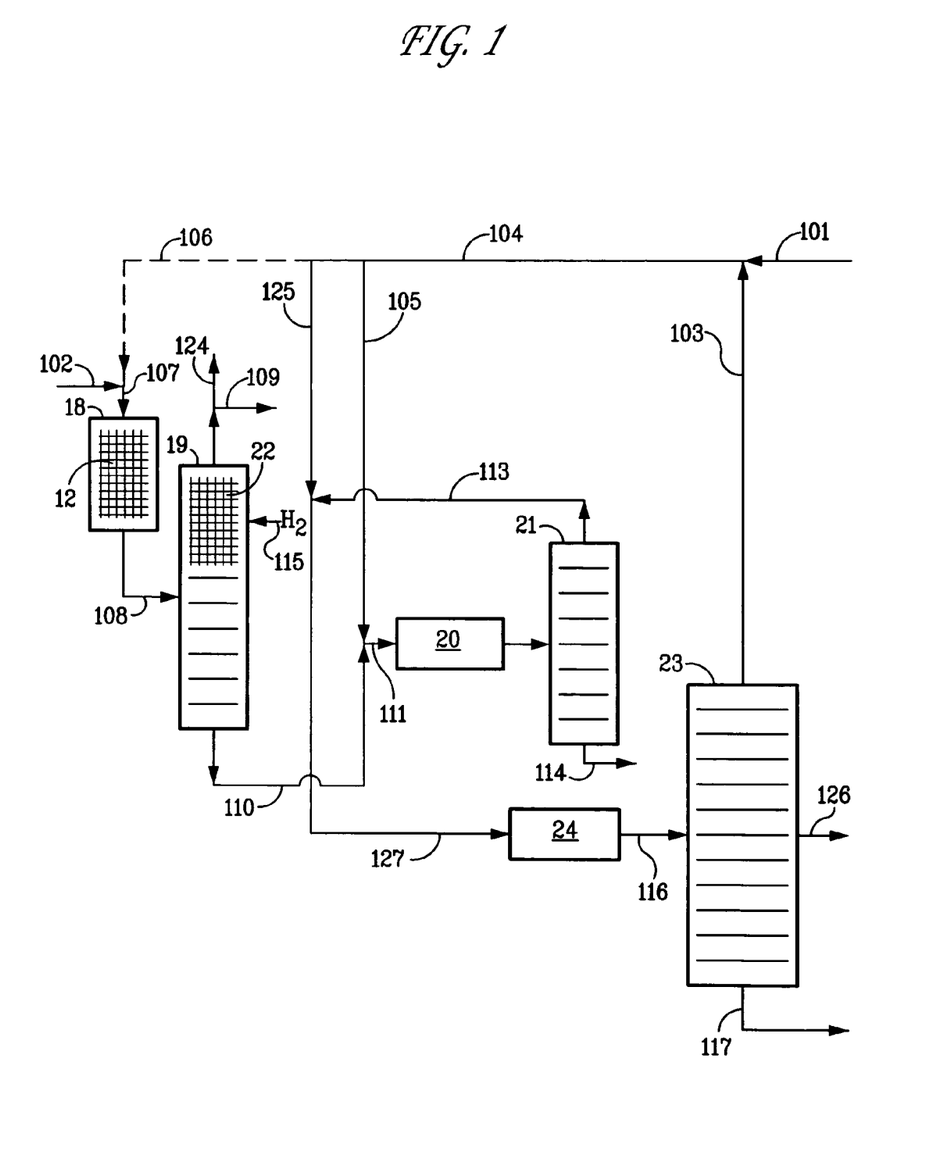
FIG. 1 is a simplified flow diagram of a basic C4 oligomerization-alkylation process.

FIG. 1 illustrates the overall process as it relates to the alkylation of an FCC $C_4$ steam with isobutane. As shown, isobutane enters the process via stream 101 and the FCC $C_4$'s enter the process via stream 102. The FCC $C_4$'s are processed prior to this step to remove any oligomerization catalyst poisons. Typically this can be accomplished by using a water wash column (not shown). The make up isobutane used for production of alkylate enters in stream 101 at a high purity, i.e. >85 vol. %. If such a stream is not available a more dilute, paraffinic, isobutane containing stream may be brought into the deisobutanizer, 23, for fractionation (not shown). The overall combined make up isobutane stream produced via the combination of streams 102 and 101 is depicted as stream 104. Stream 104, the rich isobutane stream, is then split into two streams, 105 and 106. Stream 105 is fed to a second alkylation reactor as indicated below. Stream 106 is mixed with the FCC $C_4$ stream. The reason for mixing stream 106 with the FCC $C_4$ feed stream is for use as a heat sink to handle a portion of the heat of reaction during the oligomerization step. For water-cooled oligomerization reactors it is not necessarily required and is thus optional.

The FCC $C_4$ in stream 102 stream and the optional isobutane rich stream in stream 106 are combined as stream 107 which is fed to the oligomerization reactor 18 containing a bed 12 of oligomerization catalyst. The isobutene in the FCC $C_4$ stream is oligomerized in reactor 18 to form primarily diisobutylenes and triisobutylenes along with some co-dimers leaving a $C_4$ cut rich in normal butenes. The effluent from the reactor 18 in stream 108 comprising mixed $C_4$ and oligomers is fed to distillation column 19 wherein the oligomers are separated from the unreacted $C_4$'s. If desired a bed 22 of hydrogenation catalyst may be utilized in conjunction with a hydrogen feed via stream 115 to simultaneously provide removal of the dienes in the $C_4$ stream. The removal of the dienes helps the downstream alkylation units as diene presence increases the alkylation unit catalyst consumption. The $C_4$'s ( normal butene, and isobutane), are removed as overheads, condensed and removed via stream 109 which are later fed to a first alkylation system 22. Unreacted hydrogen is vented via stream 124.

The bottoms product oligomers from reactive distillation column 19 exit in stream 110 and are mixed with isobutane rich stream 105 to form a mixed alkylation feed stream 111 which is fed to a second alkylation system 20 wherein a portion of the isobutane reacts with olefins in stream 111 to form alkylate product. The effluent from the alkylation system 20 exits as stream 112 and contains considerable isobutane along with heavier alkylate products ranging from $C_5$-$C_{16}$. Stream 112 is sent to a stripping or distillation column 21 in which the $C_4$'s are removed as overheads and product alkylate #2 is removed as stream 114. The $C_4$'s are removed as overheads via stream 113 are condensed and combined with streams 109 and 125 to form mixed stream 127 which is fed to the first alkylation unit 24 for production of alkylate by reaction with the olefins (butenes) in stream 109.

The effluent from the alkylation system 22 is removed in stream 116 and fed to a traditional deisobutanizer where alkylate product is removed as bottoms in stream 117. Normal butane is removed in side stream 126 and isobutane is removed as overheads as stream 103 which is recycled to the process.

The whole point of the process is to produce more high quality alkylate at a facility and prevent the necessity of additional deisobutanizer capacity, which is a considerably large fractionation tower requiring significant energy usage for separation. Instead, for facilities having more than one alkylation system, the need for additional deisobutanizer capacity is averted by the addition of (a) an oligomerization reactor 18, (b) a fractionation tower 19 for separation of the oligomers from unreacted C4's and (c) a fractionation tower 21 for separation of alkylate product from the second alkylation system 20. The trade off on a piece count (numbering three new pieces of equipment) is valuable in that the replacement pieces are small in size. For instance the required distillation stages for fractionators 19 and 21 can number less than eight stages each, whereas an additional deisobutanizer column will likely require 50-80 stages. This can significantly reduce overall equipment cost as less total steel is required to obtain the same quantity of motor fuel alkylate production. The process can be utilized with any type of alkylation process, solid acid alkylation, HF alkylation, sulfuric acid alkylation and combinations thereof.

Alkylation With a Mixed $C_4$/$C_5$ Olefin Feedstock

Where $C_4$ and $C_5$ feed streams are alkylated a staged alkylation system approach can be used which is similar to that shown in FIG. 1, which is characterized as a process for the alkylation of isobutane, $C_4$ and $C_5$ olefins comprising the steps of:

(a) feeding isobutane and a stream containing $C_5$ olefins to a first alkylation zone wherein a portion of the isobutane reacts with $C_5$ olefins to produce a first alkylate stream containing a first alkylate and unreacted isobutane;

(b) feeding said first alkylate to a debutanizing zone wherein the first alkylate is separated as a first bottoms from a first overheads containing the unreacted isobutane;

(c) feeding the first overheads and a stream containing $C_4$ olefins to a second alkylation zone wherein isobutane reacts with the $C_4$ olefins to produce a second alkylate stream containing a second alkylate and unreacted isobutane, (d) feeding the second alkylate stream to a deisobutanizing zone wherein the second alkylate is separated as a second bottoms from an overheads containing the unreacted isobutane. Preferably any normal butane contained in said isobutane stream passes through said first and second alkylation systems and is removed as a side stream from said deisobutanizer. Fresh isobutane may be fed to said second alkylation system to make up for that which is consumed as part of the reaction, and a portion of said first overheads may be recycled to said first alkylation system Referring now to FIG. 2 alkylation feed consisting of FCC $C_5$'s with trace amounts of n-butane (<1 vol. %) can be used wherein an interim debutanizer 250 is utilized between two alkylation systems 230 and 240 which are processing $C_5$'s and $C_4$'s respectively. It is assumed that actual separation of the $C_4$ and $C_5$ olefins (not shown) occurs upstream of FIG. 2. The $C_5$ feed is sent to the first alkylation system 230 via stream 201. The feed is mixed with the combined make up isobutane from stream 209 and the overheads from the deisobutanizer in stream 215 before being fed to the first system 230 as stream 202.

Figure 2:
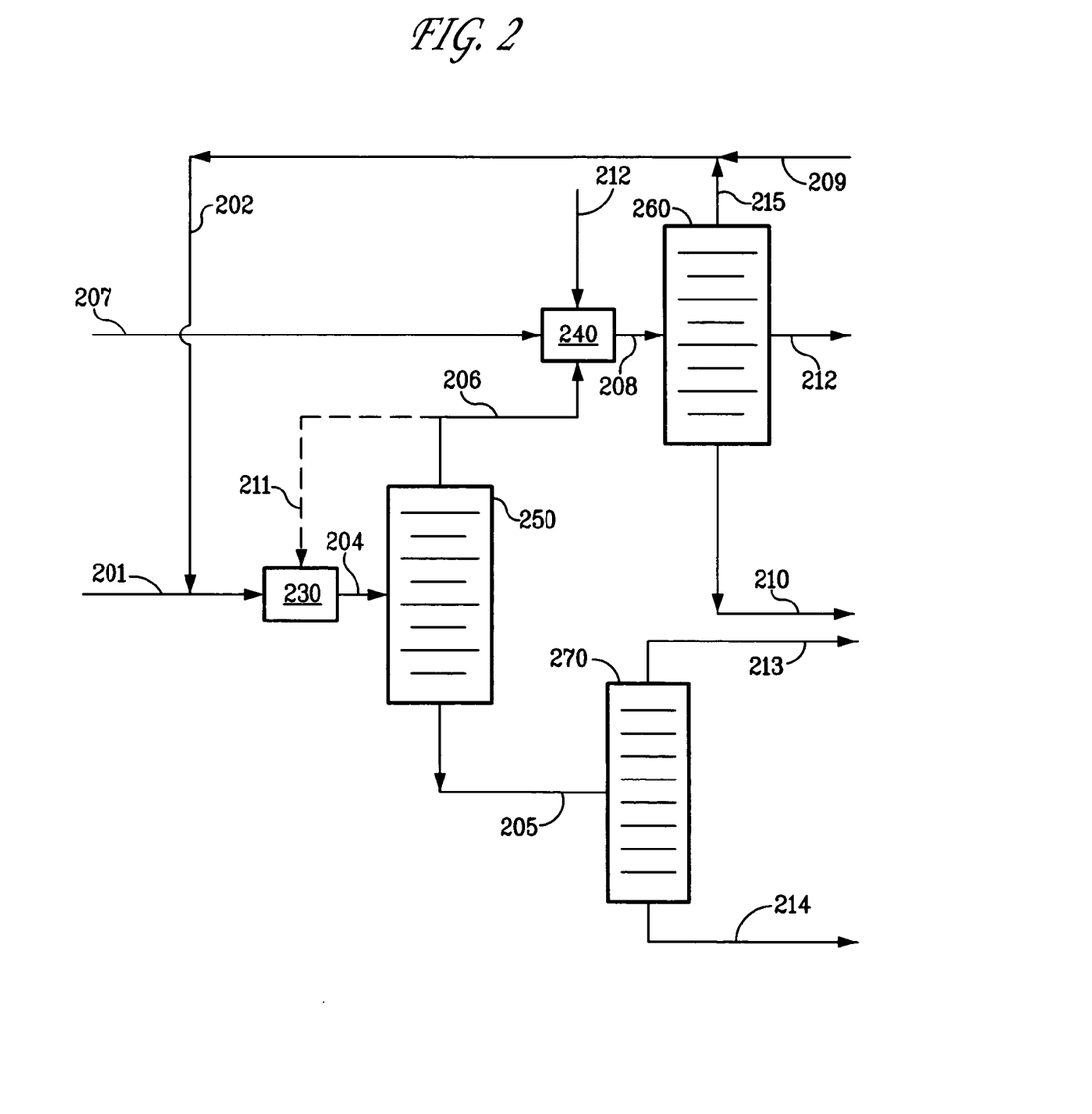
FIG. 2 is a simplified flow diagram for the alkylation of isobutane with C4 and C5 olefins.

The first alkylation system 230 is used to produce a dilute alkylate stream 204 containing a significant portion of isobutane as the primary constituent. The effluent in stream 204 is sent to debutanizer 250 which produces a bottoms alkylate stream 205. The debutanizer 250 can be a stripper or a full distillation column requiring reflux. The debutanizer is used instead of a traditional deisobutanizer to reduce the requirement of distillation stages and potentially the quantity of reflux and associated energy. The difference herein is that as the requirements are reduced away from a deisobutanizer operation, small quantities of isopentane, residing in the debutanizer overhead product are allowed to enter the second alkylation system 240. These minor quantities have a very minor effect on the overall alkylate quality obtained in alkylation system 240. Details of the effect are outlined below.

The resulting overhead stream 206 (containing primarily isobutane, a minor amount of n-butane, a small amount of isopentane and possible containing trace amounts of 2,4-dimethyl hexane and 2,2,4-trimethyl pentane) is fed along with either FCC $C_4$'s or an MTBE raffinate (containing mixed butylenes) in stream 207 to a second alkylation system 240 where they are allowed to react to produce a dilute alkylate product stream 208 in which a primary effluent constituent is isobutane. Stream 208 is then sent to a traditional deisobutanizer 260 for separation wherein an isobutane rich overhead product is removed as stream 215 and recycled to alkylation system. Alkylate product is removed as bottoms as stream 210. A normal butane rich stream is removed stream 212.

A significant variation of isobutane to olefin ratios in the two alkylation system and significant variability between alkylation for $C_4$ olefins versus alkylation from $C_5$ olefins can be achieved by utilizing flow lines 211 and 212. As one wishes to produce more alkylate from $C_4$ olefins flow line 212 is utilized. To product more alkylate product from $C_5$ olefins flow line 211 is used. The use of these flow lines stems from the alkylation system requirement to operate within a certain isobutane to olefin volumetric ratio, varying from as low as 4:1 to as high as 15:1. As quantities of alkylate production from individual $C_4$ and $C_5$ feeds vary (i.e. total volumes of $C_4$ and $C_5$ olefins vary), the need for higher volumes of isobutane for the different alkylation systems becomes necessary.

In a manner similar to the use of flow lines 211 and 212, a modification of the process shown in FIG. 1 may be made which adds an additional isobutane rich stream 125 to serve as a bypass around the oligomerization section (reactor 18 and column 19). This allows for better energy utilization as it reduces the duty on the distillation column 19. The inclusion of the bypass 125 depends on the overall isobutane to olefin ratio desired in the alkylation systems and the exit requirements (temperature, pressure, number phases) set for the oligomerization reactor 18 as discussed earlier.

The ability to produce two separate alkylate products from stream 205 may be desired. The alkylate product in stream 205 may be fractionated in column 270. The alkylate product in overhead stream 213 contains higher octane and Reid Vapor Pressure (RVP) than that in bottoms stream 214. For certain regions using $C_5$ feed stocks, this becomes a necessary step in order to produce a primary alkylate meeting RVP specifications.

Alkylation With a Mixed $C_3$/$C_4$ Olefin Feedstock

For $C_3$ olefin feedstocks the same process flow scheme as in FIG. 2 may be used. Therein $C_3$ olefin would substitute in place of the $C_5$ olefin feed. Propane in the $C_3$ feed would be taken out in a depropanizer (not shown) residing in the first alkylation system 230.

Alkylation With a Mixed $C_3$/$C_4$/$C_5$ Olefin Feedstock

Figure 3:
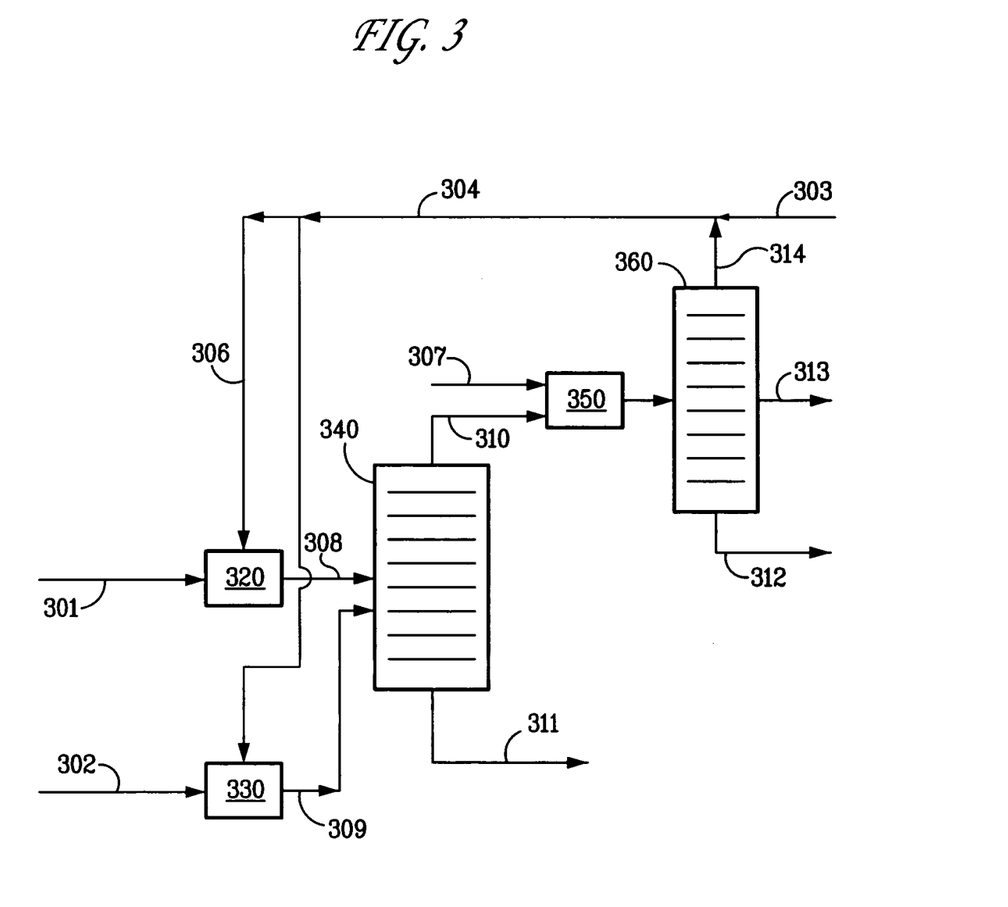
FIG. 3 is a simplified flow diagram for the alkylation of isobutane with C3, C4 and C5 olefins.

Combinations of the basic process shown in FIGS. 1 and 2 may be utilized for alkylation of a range of $C_3$-$C_4$, $C_4$-$C_5$ and $C_3$-$C_5$, olefin containing streams. FIG. 3 provides one basic option utilizing a single debutanizer 340 for alkylate effluent streams coming from olefin $C_3$ and $C_5$ feeds which have only trace amounts of normal butane in them. The $C_3$ olefin stream 301 is fed to alkylation system 320 while the $C_5$ olefin stream 301 is fed to second alkylation system 330. Make up isobutane is fed as stream 303 and recycled isobutane from deisobutanizer 360 is added as stream 314 to make combined isobutane stream 304. Isobutane is provided to first alkylation system 320 in stream 306 and to second alkylation system 330 in stream 305. As noted both effluents 308 and 309 are fed to a single debutanizer 340 with the overhead in stream 310 being fed to a third alkylation system 340 which utilized FCC $C_4$'s from stream 307 to alkylate the normal butenes in stream 310. A bottoms alkylate stream is taken from debutanizer column 340 as stream 311 and deisobutanizer 360 as stream 312.

Along these lines more involved process schemes can be derived. For instance, the $C_4$ and $C_5$ FCC feed stream may be oligomerized separately. This would allow for more flexibility in how to alkylate the olefin streams which contain only trace amounts of normal butane. Additionally the step of oligomerizing the $C_5$ stream may be deleted with the $C_5$ FCC feed being fed directly to an alkylation system and then on to the debutanizer operation. Finally a single oligomerization unit may be used for both the $C_4$'s and $C_5$'s.

A process for the alkylation of isobutane $C_3$, $C_4$ and $C_5$ olefins is characterized as comprising the steps of:

(a) feeding a first stream containing isobutane to first and second alkylation zones;

(b) feeding a second stream containing propylene to the first alkylation zone wherein the propylene reacts with a portion of the isobutane to produce a alkylate stream containing a first alkylate and unreacted isobutane;

(c) feeding a third stream containing $C_5$ olefins to the second alkylation zone wherein $C_5$ olefins react with isobutane to produce a second alkylate stream containing a second alkylate and unreacted isobutane;

(d) feeding the first and second alkylate to a debutanizing zone wherein the first and second alkylates are separated as a first bottoms from unreacted propylene and unreacted isobutane as a first overheads;

(e) feeding the first overheads and a fourth stream containing $C_4$ olefins to a third alkylation zone wherein the $C_4$ olefins react with a portion of the unreacted isobutane in the first overheads to produce a third alkylate stream containing a third alkylate and unreacted isobutane;

(f) feeding the third alkylate stream to a deisobutanizing zone wherein the third alkylate is separated as a second bottoms from the unreacted isobutane as a second overheads. Preferably any normal butane contained in said isobutane stream passes through said first, second and third alkylation systems and is removed as a side stream from said deisobutanizer and the isobutane contained within said second overheads is recycled to said first and second alkylation systems Staging and Energy From a distillation perspective the invention is basic. Reducing the overhead specification to include minor amount of $C_5$ materials loosens the overall design requirements as compared to a traditional deisobutanizer, allowing for a substantial decrease in distillation column stages and optionally some reduction in column diameter, and condensing duty. The use of an inter-stage debutanizer between two alkylation units to reduce the need for additional deisobutanizer capacity when expanding a $C_4$ MTBE raffinate alkylation operation to a full FCC $C_4$ operation, a $C_4$ alkylation operation into a $C_3$ and $C_4$ operation, a $C_4$ operation into a $C_4$ and $C_5$ operations or a $C_4$ operation into a $C_3/C_4/C_5$ operation, has not been heretofore described in the prior art. In the end, some amount of deisobutanizer capacity is required for the entire alkylation process flow scheme so that trace amounts of normal butane found in various feed streams (isobutane make up, olefin feeds, etc.) are not allowed to build up in the system. The invention reduces the overall deisobutanizer requirement necessary as compared with the traditional use of multiple deisobutanizers as depicted in U.S. Pat. No. 5,648,586.

Fundamental calculations can be made for comparison of a traditional expansion using two deisobutanizers for $C_4$ and $C_5$ alkylation (see U.S. Pat. No. 5,648,586) versus an expansion as disclosed herein as FIG. 2. The two cases can be compared by simple distillation calculations for the effluent from the alkylation system which produces a dilute alkylate stream. A typical dilute alkylate stream is used for comparing the new scheme versus the traditional scheme for $C_5$ olefin feed containing isopentane and n-pentane. The dilute alkylate product composition as produced from an FCC $C_5$ feedstock and a recycle isobutane stream, and a dilute alkylate product produced form alkylating a $C_3$ olefin feed and isobutylene feed is provided in TABLE I.

Information presented by Kranz & Albright, "Alkylation of Isobutane with Pentenes Using Sulfuric Acid as a Catalyst: Chemistry and Reaction Mechanisms". *Ind. Chem. Res.* 1992, 31, pp 475-481, was used as a basis for the $C_3$ and isobutylene ($iC_4=$) cases. Although isobutylene is present herein it presents the basis used to represent the diisobutylene case shown in FIG. 1. US2004/017901 teaches that due to the de-polymerization behavior of diisobutylene, oligomers of isobutylene act essentially like isobutylene on a weight basis in an alkylation system.

TABLE 1

DILUTE ALKYLATE STREAMS FROM OLEFIN FEEDS

| Component, wt fraction | $C_5$ = Alky effluent | $C_3$ = Alky effluent | $iC_4$ = Alky effluent |
|---|---|---|---|
| Propane | 0.004 | 0.004 | 0.004 |
| $iC_4$ | 0.589 | 0.530 | 0.536 |
| $nC_4$ | 0.062 | 0.056 | 0.056 |
| $iC_5$ | 0.109 | 0.012 | 0.032 |
| $nC_5$ | 0.014 | 0.000 | 0.000 |
| $C_6$'s | 0.033 | 0.016 | 0.023 |
| $C_7$'s | 0.006 | 0.276 | 0.023 |
| TMP | 0.044 | 0.048 | 0.218 |
| DMH | 0.009 | 0.008 | 0.034 |
| $C_9$'s | 0.084 | 0.005 | 0.023 |
| $C_{10}$'s | 0.018 | 0.036 | 0.017 |
| $C_{11}$'s | 0.005 | 0.008 | 0.031 |
| $C_{12}$'s | 0.021 | 0.002 | 0.038 |

TABLE II provides the results of the comparison between the present interim debutanizer operation and a typical, prior art deisobutanizer operation for the three major feed cases: $C_5=$, $C_3=$ and $iC_4=$. The basis for these cases was to produce an alkylate product having less than a 5 psia RVP maximum. Distillation overhead pressure was set to 100 psia and the overall design was chosen to be at a factor of 1.2 times the minimum reflux requirement. The feed to the columns entered as a liquid at 100° F.

For each feed case two interim options are listed, each having a different control isopentane allowed in the overhead product. The "interim" stripper provides the lowest energy and staging option to meet the minimum RVP case of 5 psia, and thus allows a variable quantity of isopentane (present in the feed) to come out in the overhead product. The "interim" debutanizer case uses a maximum overhead isopentane specification of 0.25 wt % and limits $C_4$'s in the alkylate product to meet at minimum of a 5 psia RVP. It also requires an associated higher quantity of duty and staging to meet these specifications when compared to the stripper case.

To an extent, the "interim" cases provide the range of operation in which an interim debutanizer operation may be configured for each of the feeds given in TABLE I. As feed composition changes variations of course exist. For the most part TABLE II provides a good view of the possible options and thus the basis for selecting the appropriate process for such a flow scheme for a $C_5$, $C_3$ and isobutylene feed.

In terms of distillation staging required there is no comparison between traditional deisobutanizer requirements and the "interim" alkylation staging operations. Staging for all interim cases is always less due to the key components chosen for separation. Energy requirements for the "interim" cases with the present debutanizer operations typically require slightly higher duty as compared to traditional well designed deisobutanizer cases and with slightly lower duties required for the stripper cases. TABLE III provides a list comparing the relative staging required and relative energy require for the various "interim" options comparing the traditional debutanizer, interim stripper and interim debutanizer.

TABLE II

DEBUTANIZER/STRIPPER/DEISOBUTANIZER COMPARISON

|  | Reboiler Duty (BTU/Hr) | Minimum Reflux Ratio | Minimum Stages | Actual Reflux Ratio | Actual Stages | Alkylate RVP(psia) | Isopentane Wt % in OH | nC5 Wt5 in OH |
|---|---|---|---|---|---|---|---|---|
| $C_5$ = Feed case ||||||||| 
| Deisobutanizer | 3.48E+07 | 0.47 | 33 | 0.57 | 84 | To debut and depent | 0.00 | 0.00 |
| Interim C4 Stripper | 3.07E+07 | — | — | 0 | 10 | 5 | 11.30 | 1.00 |
| Interim debutanizer | 4.18E+07 | 0.76 | 15 | 0.90 | 35 | to depent | 0.25 | 0.00 |
| $C_3$ = Feed Case ||||||||| 
| Deisobutanizer | 3.90E+07 | 0.47 | 33 | 0.57 | 84 | To debut | 0.00 |  |
| Interim C4 Stripper | 3.30E+07 | — | — | 0 | 10 | 2.7 | 0.72 |  |
| Interim debutanizer | 4.04E+07 | 0.44 | 11 | 0.53 | 28 | 3.0 | 0.25 |  |
| $iC_4$ = Feed Case ||||||||| 
| Deisobutanizer | 3.97E+07 | 0.47 | 33 | 0.57 | 84 | to debut | 0.00 |  |
| Interim C4 Stripper | 3.35E+07 | — | — | 0 | 10 | 2.8 | 1.30 |  |
| Interim debutanizer | 4.57E+07 | 0.65 | 13 | 0.78 | 31 | 3 | 0.25 |  |

TABLE III

|  | Relative Duty | Relative No. of Stages |
|---|---|---|
| $C_5$ = Feed Case |||
| Deisobutanizer | 1.00 | 1.00 |
| Interim C4 Stripper | 0.88 | 0.12 |
| Interim debutanizer | 1.20 | 0.42 |
| $C_3$ = Feed Case |||
| Deisobutanizer | 1.00 | 1.00 |
| Interim C4 Stripper | 0.85 | 0.12 |
| Interim debutanizer | 1.04 | 0.33 |
| $iC_4$ = Feed Case |||
| Deisobutanizer | 1.00 | 1.00 |
| Interim C4 Stripper | 0.84 | 0.12 |
| Interim debutanizer | 1.15 | 0.37 |

From just an energy and staging requirement, the stripper case is always preferred with a choice between traditional deisobutanizer and interim debutanizer becoming a clear tradeoff between energy and staging and thus an operational cost versus initial capital cost consideration. A significant difference is that the interim designs allow some introduction of isopentane into a secondary alkylation system.

It has been found that the addition of isopentane to an alkylation system using FCC $C_4$ feed can cause reduced product octane if not properly controlled. As isopentane is limited to a number as low as 0.25 Wt % the difference in octane numbers between feed with and without isopentane becomes immeasurable due to the available precision of typical octane tests. This allows better comparison of the options of traditional deisobutanizer with interim debutanizer on nearly equivalent terms, with the exception that the interim case provides for production of an alkylate product meeting RVP requirement.

It is anticipated that (1) with the use of more low pressure steam available for heating, (2) the use of available process streams for feed heating, and (3) the new retro fit options that are allowed due to the reduced staging requirements, a likely choice for a refiner between an interim debutanizer operation and a traditional deisobutanizer will be that of the interim debutanizer as a means to increase their overall alkylation capacity. For the case of $C_3$ olefin feed as shown in TABLE III the interim options are clearly beneficial, with the stripper case having 12% of the staging, 85% of the energy and only 0.73 wt % isopentane in the overhead product due to the limited make of isopentane in the first alkylation system.

For the comparison made, the deisobutanizer case does not include the total duty required for production of an alkylate product, whereas for all interim cases, except the debutanizer $C_5$= case, the associated duty provided allows for production of an alkylate product. For the $C_5$= case, the feed contains so much isopentane that the debutanizer bottoms stream requires the use of a depentanizer to meet the alkylate RVP requirement. Thus additional equipment is required for that case. This is also true for the traditional deisobutanizer case.

Effect of Isopentane on a Secondary Alkylation System

Figure 4:
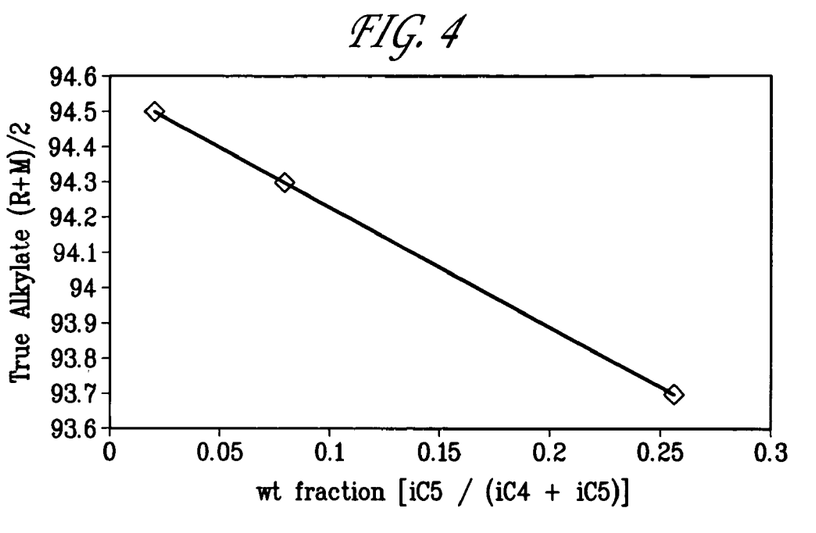
FIG. 4 is a plot of alkylate quality as a function of isopentane in the feed.
Figure 5:
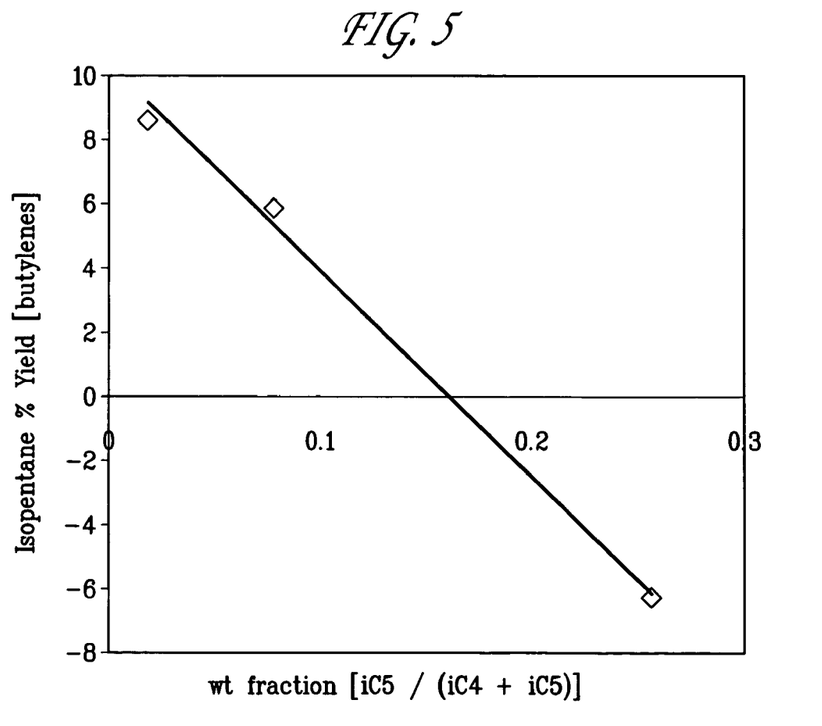
FIG. 5 is a plot of isopentane yield as a function of isopentane in the feed.

As pointed out above, the fundamental effect of isopentane on product quality needs to be quantified. This was accomplished by performing an experiment wherein a mixture of isobutane and isopentane was co-fed with an FCC $C_4$ olefin to produce an associated alkylate product. The results are shown in FIGS. 4 and 5. As shown in FIG. 4, increased isopentane in the feed causes a drop in alkylate quality as measured by the true (research+motor octane)/2 number as produced at a constant olefin space velocity, total isoparaffin/olefin ratio, temperature and mixing energy. Comparing an overhead stream in the range of around 8% $iC_5$ in the $iC_5$-$iC_4$ mixture to one with none, only a slight drop in quality is seen, between 0.2-0.3 octane points. Within this range such quality effects are slight in comparison to the quality effects associated with the overall alkylation system operation (OSV, I:O etc). Also it can be found from FIG. 5 that the cause for the reduction in octane up and (to some extent) beyond 8% is due rather to dilution of the alkylate with isopentane rather than any significant conversion of isopentane during the alkylation process. This slight drop in quality is also offset in the scheme shown herein because isopentane, which is transferred to the next stage of alkylation (possibly reducing the overall octane of the second alkylate product) can consequently provide for the lower RVP and higher quality alkylate product in the first alkylation stage, depending on the base alkylate blending properties.

A particular finding, during the measurement of the effect of isopentane on product quality (FIG. 4), is that the net isopentane consumption (using an FCC C4 feedstock) does not occur until the $iC_5/(iC_5+iC_4)$ weight ratio is beyond 8 wt %. Indeed, contrary to a range of conditions listed in earlier studies (U.S. Pat. No. 5,583,275) it has been found that sulfuric acid catalyzed alkylation (run at low temperatures of from 25-35° F., with acid strengths between 92-98 wt %) the incorporation of isopentane into alkylate is much reduced relative to isobutane, thus preventing overall consumption at the feed conditions. It was found and plotted in FIG. 4 that an $iC_5/(iC_5+iC_4)$ ratio of <0.1 provides for a net yield or net make of isopentane when using an FCC $C_4$ feedstock which is directly opposite to that disclosed in U.S. Pat. No. 5,583,275.

The invention claimed is:

1. A process for the alkylation of isobutane with an olefin comprising:
   (a) feeding a first stream comprising an FCC hydrocarbon stream comprising an olefin to an oligomerization reactor, wherein at least a portion of the olefins react with each other to produce an effluent containing olefin oligomers;
   (b) fractionally distilling the effluent from the oligomerization reactor wherein unreacted $C_4$ olefins and lighter materials are separated as a first overheads from $C_5$ and heavier oligomers as a first bottoms;
   (c) feeding the first bottoms and a second stream containing isobutane to a first alkylation system where a portion of the isobutane is reacted with a portion of the olefin oligomers to form an effluent comprising a dilute alkylate stream;
   (d) feeding the effluent from the first alkylation system to a debutanizer where $C_4$'s are removed as a second overheads and a first alkylate product is removed as a second bottoms;
   (e) feeding the first overheads and the second overheads to a second alkylation system where isobutane is reacted with $C_4$ olefins in said first overheads and said second overheads to form a second alkylate product.

2. The process according to claim 1 wherein said first stream comprises an FCC $C_4$ stream containing normal butene, isobutene, normal butane and isobutane.

3. The process according to claim 1 where said first stream contains a mixture of $C_4$ and $C_5$ olefins.

4. The process according to claim 1 wherein said first stream contains a mixture of $C_3$ and $C_4$ olefins.

5. The process according to claim 1 wherein said first stream contains a mixture of $C_3$, $C_4$ and $C_5$ olefins.

6. The process of claim 1, further comprising feeding a third stream containing isobutane to the second alkylation system.

7. The process of claim 1, further comprising
   (f) feeding the second alkylate stream to a deisobutanizing zone wherein isobutane is removed as a third overheads, alkylate is removed as a third bottoms and normal butane is removed as a side stream.

8. The process of claim 1, further comprising feeding at least one of an FCC C3 and an FCC C5 stream to the first alkylation system.

9. A process for the alkylation of isobutane with butenes contained in an FCC $C_4$ stream comprising the steps of:
   (a) feeding a first stream comprising an FCC $C_4$ stream containing normal butenes and isobutenes to an oligomerization reaction wherein the isobutenes react with each other to produce an effluent containing $C_5$ and higher oligomers and normal butenes;
   (b) fractionally distilling the effluent from the oligomerization reaction wherein the $C_4$ and lighter material is separated as a first overheads from the $C_5$ and heavier material as a first bottoms;
   (c) feeding the first bottoms and isobutane to a first alkylation zone to produce a first alkylate stream containing alkylate and unreacted $C_4$'s;
   (d) feeding the first alkylate stream to a debutanizing zone wherein the unreacted $C_4$'s are removed as a second overheads and alkylate product is removed as a second bottoms;
   (e) feeding the first overheads and isobutane to a second alkylation zone wherein the olefins in the first overheads are reacted with isobutane to produce a second alkylate stream containing alkylate, unreacted isobutane and unreacted normal butane;
   (f) feeding the second alkylate stream to a deisobutanizing zone wherein isobutane is removed as a third overheads, alkylate is removed as a third bottoms and normal butane is removed as a side stream.

10. The process according to claim 9 wherein isobutane is fed as a second stream to the oligomerization reaction.

11. The process according to claim 10 wherein the third overheads is combined with said second stream and fed to the oligomerization reaction.

12. The process according to claim 9 where dienes contained within said effluent are hydrogenated simultaneously with the fractional distillation in a bed of hydrogenation catalyst with hydrogen.

13. The process according to claim 9 wherein fresh isobutane is fed to said second alkylation zone.

14. The process of claim 9, further comprising feeding the second overheads to the second alkylation zone.

15. A process for the alkylation of isobutane with $C_4$ and $C_5$ olefins comprising the steps of:
   (a) feeding a stream containing $C_5$ olefins to an oligomerization reactor, wherein the olefins react with each other to produce an effluent containing $C_5$'s and heavier oligomers;
   (b) feeding at least a portion of the oligomerization reactor effluent and isobutane to a first alkylation zone wherein a portion of the isobutane reacts with $C_5$ oligomers to produce a first alkylate stream containing a first alkylate and unreacted isobutane;
   (c) feeding said first alkylate to a debutanizing zone wherein the first alkylate is separated as a first bottoms from a first overheads containing the unreacted isobutane;
   (d) feeding the first overheads and a stream containing $C_4$ olefins to a second alkylation zone wherein isobutane reacts with the $C_4$ olefins to produce a second alkylate stream containing a second alkylate and unreacted isobutene;
   (e) feeding the second alkylate stream to a second debutanizing zone wherein the second alkylate is separated as a second-bottoms from a second overheads containing the unreacted isobutane.

16. The process according to claim 15 wherein any normal butane contained in said isobutane stream passes through said first and second alkylation zones and is removed as a side stream from said deisobutanizing zone.

17. The process according to claim 15 wherein said first bottoms containing said first alkylate is fed to a fractional distillation wherein the first alkylate is separated into a third and fourth alkylate.

18. The process according to claim 15 wherein fresh isobutane is fed to said second alkylation zone.

19. The process according to claim 15 wherein a portion of said first overheads is recycled to said first alkylation zone.

20. The process according to claim 15, further comprising feeding a stream comprising $C_3$ olefins to at least one of the first alkylation zone and the second alkylation zone.

21. A process for the alkylation of isobutane with $C_3$, $C_4$ and $C_5$ olefins comprising the steps of:
  (a) feeding a first stream containing $C_4$ olefins to an oligomerization reactor, wherein the olefins react with each other to produce an effluent containing oligomers;
  (b) feeding isobutane and a second stream containing at least one of propylene and isopentenes to a first alkylation zone wherein the propylene, isopentenes, or both reacts with a portion of the isobutane to produce an alkylate stream containing a first alkylate and unreacted isobutane;
  (c) feeding the first alkylate to a debutanizing zone wherein the first alkylate is separated as a first bottoms from unreacted propylene and unreacted isobutane as a first overheads;
  (d) feeding the first overheads and at least a portion of the oligomerization reactor effluent to a second alkylation zone wherein the oligomers react with a portion of the unreacted isobutane in the first overheads to produce a second alkylate stream containing a second alkylate and unreacted isobutane;
  (e) feeding the second alkylate stream to a deisobutanizing zone wherein the second alkylate is separated as a second bottoms from the unreacted isobutane as a second overheads.

22. The process according to claim 21 wherein any normal butane contained in said isobutane stream passes through said first, second and third alkylation zones and is removed as a side stream from said deisobutanizing zone.

23. The process according to claim 21 wherein the isobutane contained within said second overheads is recycled to said first and second alkylation zones.

24. The process according to claim 21, further comprising oligomerizing at least one of the $C_3$ and $C_5$ olefins prior to feeding to the first alkylation zones.

* * * * *